United States Patent [19]
Borland et al.

[11] Patent Number: 5,055,233
[45] Date of Patent: Oct. 8, 1991

[54] DETERGENT BAR PROCESS USING TRIALKYLAMINE OXIDE DIHYDRATE

[75] Inventors: James E. Borland; Kim R. Smith, both of Baton Rouge, La.

[73] Assignee: Ethyl Corporation, Richmond, Va.

[21] Appl. No.: 415,886

[22] Filed: Oct. 2, 1989

Related U.S. Application Data

[63] Continuation-in-part of Ser. No. 344,275, Apr. 26, 1989, abandoned.

[51] Int. Cl.$^5$ .................. C11D 1/75; C11D 17/00
[52] U.S. Cl. .................. 252/547; 252/117; 252/134; 252/132; 252/DIG. 16; 252/174; 252/517
[58] Field of Search .............. 252/117, 542, 134, 132, 252/174, DIG. 16, 547; 564/298

[56] References Cited

U.S. PATENT DOCUMENTS

| | | | |
|---|---|---|---|
| 3,202,714 | 8/1965 | Zimmerer et al. | 252/117 |
| 3,223,647 | 12/1965 | Drew et al. | 252/117 |
| 3,312,627 | 4/1967 | Hooker | 252/547 |
| 4,320,033 | 3/1982 | Yoshikawa | 252/174 |
| 4,748,275 | 5/1988 | Smith et al. | 564/298 |
| 4,960,934 | 10/1990 | Smith et al. | 546/192 |

*Primary Examiner*—David L. Lacey
*Assistant Examiner*—Thomas E. Daley
*Attorney, Agent, or Firm*—Joseph D. Odenweller; Patricia J. Hogan

[57] ABSTRACT

Detergent bars suitable for use as toilet soaps are made by mixing an effective amount of a trialkylamine oxide dihydrate in a detergent bar formulation.

9 Claims, No Drawings

DETERGENT BAR PROCESS USING TRIALKYLAMINE OXIDE DIHYDRATE

PRIOR APPLICATIONS

This application is a continuation-in-part of application Ser. No. 344,275, filed Apr. 26, 1989, now abandoned.

BACKGROUND

Trialkylamine oxides are known to have excellent foaming properties which would render their use in toilet bars highly desirable (Kamen et al. U.S. Pat. No. 3,562,167). Such trialkylamine oxides are conventionally made by reacting a trialkylamine having at least one detergent range alkyl group with aqueous hydrogen peroxide. The trialkylamine oxide that forms has a tendency to form gels in the aqueous reaction medium. Because of this, it has been necessary in the commercial production of trialkylamine oxides to limit their concentrations to no more than about 30 weight percent (e.g., Ammonyx LO, 30 weight percent aqueous lauryl dimethylamine oxide, Onyx Chemical Co.). Attempts to form a more highly concentrated product causes the reaction mixture to gel making it essentially unstirrable. Because of this, use of trialkylamine oxides in applications where water addition must be limited is prohibited. Such applications are exemplified by use. The addition of only 10 weight percent trialkylamine oxide as a 30 percent aqueous solution would concurrently introduce about 23 weight percent water into the detergent bar resulting in a paste which would require further drying. The only known alternative would be to remove water from the trialkylamine oxide solution either before mixing it with the other components in the formulation which appears to be the method used in Poper et al. U.S. Pat. No. 4,290,904, because Ammonyx LO used in its examples is a commercial 30 weight percent lauryl dimethylamine oxide solution sold at one time by Onyx Chemical Co., or, after blending it with the other components, followed by a water removal step, as shown in Yoshikawa U.S. Pat. No. 4,320,033. These alternate methods are high energy consumers leading to a prohibitive economic penalty. A need exists for a process for making detergent bars containing detergent range trialkylamine oxide without the use of dilute aqueous solutions of the trialkylamine oxides and without the necessity of driving off large amounts of water from the heat sensitive trialkylamine oxide solution or from the toilet bar formulation made with it.

SUMMARY

According to the present invention, detergent bars useful as toilet bars such as facial soap or in other personal hygiene applications can be made by mixing certain trialkylamine amine oxide dihydrates with other conventional detergent bar components and molding or extruding and stamping the mixture into toilet soap bar form.

DESCRIPTION OF THE PREFERRED EMBODIMENTS

A preferred embodiment of the invention is a method of making a detergent bar suitable for use as toilet soap, said method comprising mixing trialkylamine oxide dihydrate having the structure:

$$R'R''R'''NO \cdot 2H_2O$$

wherein $R'$ is a primary alkyl containing 8-24 carbon atoms, $R''$ is methyl, ethyl or a primary alkyl containing 8-24 carbon atoms and $R'''$ is methyl or ethyl, into a detergent bar formulation in an amount to provide about 5-80 of resultant detergent bar.

The essential trialkylamine oxide dihydrates can be made by the process described in application Serial No. 344,275, filed Apr. 26, 1989, now abandoned. According to that process, the appropriate amine is reacted with at least a stoichiometric amount of concentrated (e.g., 50-70 weight percent active) hydrogen peroxide in an organic ester solvent (e.g., ethyl acetate) in an amount sufficient to maintain a fluid reaction mixture. Reaction temperatures of about 25°-100° C. can be used. A preferred range is 60°-75° C. Carbon dioxide can be injected to promote the reaction. Use of about 1.2 theories of 70 weight percent hydrogen peroxide results in a final reaction mixture which contains about 2 moles of water per mole of amine oxide. If more water than this is present, it should be distilled out to obtain a 2/1 water/amine oxide mole ratio. The organic ester solution can then be cooled causing the amine oxide dihydrate to crystallize. Alternatively, the organic ester can be distilled out at atmospheric pressure or under vacuum to obtain the amine oxide dihydrate as the residue. It was surprisingly found that the tert-amine oxide dihydrate was not hygroscopic.

Trialkylamines useful in making the tert-amine oxide dihydrate are those having the formula $R'R''R'''N$ wherein $R'$ $R''$ and $R'''$ are as previously defined. Representative examples of these are:

n-octyl diethylamine
n-decyl dimethylamine
n-decyl diethylamine
n-dodecyl dimethylamine
n-dodecyl diethylamine
n-tetradecyl dimethylamine
n-hexadecyl diethylamine
n-octadecyl dimethylamine
n-eicosyl dimethylamine
di-(n-octyl)methylamine
di-(n-decyl)methylamine
di-(n-dodecyl)ethylamine
di-(n-tetradecyl)methylamine
di-(n-hexadecyl)ethylamine
di-(n-octadecyl)methylamine
di-(n-eicosyl)methylamine
n-octyl n-dodecyl methylamine
n-decyl n-octadecyl ethylamine
n-decyl n-eicosyl ethylamine and the like including mixtures thereof.

Of the above, a still more preferred class of tertamines consists of those in which $R'$ is a $C_{8-24}$ primary alkyl, $R''$ is methyl or a $C_{8-24}$ primary alkyl and $R'''$ is methyl. Examples of these are:

octyl dimethylamine
decyl dimethylamine
dodecyl dimethylamine
tetradecyl dimethylamine
hexadecyl dimethylamine
eicosyl dimethylamine
docosyl dimethylamine
tetracosyl dimethylamine
dioctyl methylamine
didecyl methylamine
didodecyl methylamine decyl dodecyl methylamine
ditetradecyl methylamine
tetradecyl octyl methylamine
and the like including mixtures thereof.

The following Examples show how to make the required trialkylamine oxide dihydrate.

EXAMPLE 1

In a 250 milliliter glass reaction flask was placed 100 grams of tetradecyldimethylamine (0.41 mole; amine value 230.0 mg KOH/g amine) and 0.5 gram (1.27 mmol) of diethylenetriaminepentaacetic acid. This was heated with stirring to 65° C. and then 23 grams (0.47 mole) of 70 weight percent aqueous hydrogen peroxide was added dropwise over a 15-minute period. The mixture was then heated to 76° C. and stirred at that temperature for seven hours. As needed, ethyl acetate (34 mL) was added dropwise to the reaction mass in order to maintain a clear, gel-free liquid. Analysis of the crude reaction mass showed 99 percent amine conversion by proton NMR. The crude reaction mass was added to 400 mL additional ethyl acetate. The solution was then cooled to 15° C. forming a non-hydroscopic white crystalline solid tetradecyldimethylamine oxide dihydrate in 86% recovered yield melting at about 41° C.

EXAMPLE 2

In a glass reaction flask was placed 100 g tetradecyl dimethylamine and 0.5 g diethylenetriamine pentaacetic acid. Carbon dioxide sparge into the liquid phase was started and the mixture was stirred and heated to 65° C. The $CO_2$ sparge was stopped and a $CO_2$ gas phase was maintained over the reaction mixture. Dropwise feed of 70 weight percent aqueous hydrogen peroxide was started. At the same time, addition of ethyl acetate was commenced. After 10 minutes all the hydrogen peroxide and 28 mL of ethyl acetate had been added. Cooling was required to maintain the temperature under 75° C. Heat was applied and the reaction continued for two more hours. Dropwise addition of ethyl acetate was continued for the first 19 minutes of the two-hour period. Total ethyl acetate feed was 43 mL. The reaction mixture was a clear gel-free solution. The reaction mixture was analyzed by NMR showing a 100 percent amine conversion. The reaction mixture was poured into a flask containing 300 mL of ethyl acetate and cooled to 15° C. Needle-like crystals of tetradecyl dimethylamine oxide dihydrate form (106 g) indicating a 87 percent yield.

The amount of the trialkylamine oxide dihydrate in the detergent bar can vary from about 5-80 weight percent. A preferred amount is about 10-50 weight percent and most preferably 25-40 weight percent.

Other components can optionally be included in the detergent bar formulation. These include glycerol or other polyol moisturizers, fragrance, bactericide, fungicide, dye, fatty acids (e.g., stearic acid), polyglycols, alkanol amines (e.g., triethanol amines), witch hazel, citric acid, opalescent agents, opacity agents, water, and the like.

It is also common practice to include fatty acid soaps in detergent bars. When used in the present invention, the resultant detergent bar is referred to as a "combar" meaning it contains the combination of a fatty acid soap and a synthetic detergent. Useful fatty acids are those in the so-called detergent range of $C_{12}$ to $C_{18}$ such as tallow acid, oleic acid, stearic acid, coco acid and the like. Neutralizing agents include alkali metal hydroxides and tert-amines such as tri-ethanol amine, coco diethanol amine, and the like. The amount of fatty acid soap in a combar can range from about 10 to 90 weight percent.

Other synthetic detergents may be used in combination with the present trialkylamine oxide dihydrates. These include sodium cocyl N-methyl tauride, tallow ester of sodium isethionate, sodium oleylsulfate, sodium monolauryl sulfosuccinate, sodium salt of mono-oleic acid ester of glycerol sulfate, sodium lauryl sulfoacetate, sodium isostearoyl-2-lactylate, sodium cocyl isethionate, lauryl diethanolamide.

The amount of synthetic detergent other than the trialkylamine oxide dihydrate in the toilet bar can vary widely from none to about 80 weight percent. A useful range is about 10-75 weight percent.

The toilet bar can be made using both a fatty acid soap and a synthetic detergent other than trialkylamine oxide dihydrate.

The trialkylamine oxide dihydrate can be mixed with the other ingredients in the detergent bar formulation by any of the known procedures. After the trialkylamine oxide dihydrate is blended into the formulation, the mixture should not be heated over about 120° C. and preferably not over 100° C. The trialkylamine oxide decomposes at elevated temperatures.

A useful method to prepare the formulation is to pre-mix all ingredients that require drying such as the wet soap noodles and to heat this pre-mixture to drive off water to the desired water content (ca 10%). The dehydrated mixture is then fed to a 3-roll mill together with the trialkylamine oxide dihydrate and any other ingredients desired and the mixture is thoroughly blended. The blended mixture is extruded in a plodder to form an elongated log. The elongated log is cut into soap bar size segments and each segment is placed in a two-piece mold which is compressed to form the final detergent bar.

The trialkylamine oxide dihydrates may be added as a liquid or as a solid. The low carbon number dihydrates are liquids under ambient conditions. For example, octyl dimethylamine oxide dihydrate melts at about 15° C. Decyl dimethylamine oxide dihydrate melts at 22°-23° C. The more preferred $C_{12}$ and higher alkyl dimethylamine oxide dihydrates melt above 30° C. For example, n-dodecyl dimethylamine oxide dihydrate melts at 30°-31° C., tetradecyl dimethylamine oxide dihydrate melts at 41°-42° C., hexadecyl dimethylamine oxide dihydrate melts at 49°-50° C. and octadecyl dimethylamine oxide dihydrate melts at 61°-62° C.

The solid amine oxide dihydrates may be added as a solid, e.g., crystals, flakes or chunks, or may be melted and added in molten form.

The following Examples show how to make the detergent bars containing the present trialkylamine oxide dihydrate by the process of the present invention. All parts are by weight.

EXAMPLE 3

To a 3-roll mill is fed n-tetradecyl dimethylamine oxide dihydrate and a sodium fatty acid (70/30 tallow-coco acid) soap (10 weight percent water) in a weight ratio of 5:95. The mixture is thoroughly blended in the mill and then extruded through a plodder to form an elongated 1½ inches in diameter. The log is cut into 3-inch segments, each of which is placed into one cavity of 2-piece mold. The mated mold member is compressed to form the finished soap bar.

EXAMPLE 4

In a crutcher mixing vessel is placed 10 parts of a sodium fatty acid (70/30 tallow/coco acids) soap containing 10 weight percent water, 60 parts sodium cocoyl isetheonate, 5 parts stearic acid and 25 parts tetradecyl dimethylamine oxide dihydrate. The mixture is passed through a plodder and extruded to form noddles. The noodles are further blended in a multi-roll mill and the milled sheet again proccessed through a plodder and extruded in a ribbon form. The ribbon is cut into segments approximating the size of the desired toilet bar and each segment is stamped to final form.

A series of formulations were prepared following the above generally procedure. The following Table shows the components blended to make each formulation:

TABLE

| | Examples | | | | | | | | | | | | | | |
|---|---|---|---|---|---|---|---|---|---|---|---|---|---|---|---|
| | 2 | 3 | 4 | 5 | 6 | 7 | 8 | 9 | 10 | 11 | 12 | 13 | 14 | 15 | 16 |
| Tetradecyl dimethyl amine oxide dihydrate | 50 | 95 | 5 | 50 | 95 | 5 | 50 | 95 | 5 | 50 | 95 | 5 | 50 | 95 | 5 |
| Soap | 50 | 5 | 0 | 0 | 0 | 0 | 0 | 0 | 0 | 0 | 0 | 0 | 0 | 0 | 0 |
| Igepon AC-78[1] | 0 | 0 | 95 | 50 | 5 | 0 | 0 | 0 | 0 | 0 | 0 | 0 | 0 | 0 | 0 |
| Igepon TC-42[2] | 0 | 0 | 0 | 0 | 0 | 95 | 50 | 5 | 0 | 0 | 0 | 0 | 0 | 0 | 0 |
| Sodium dodecyl benzene sulfonate | 0 | 0 | 0 | 0 | 0 | 0 | 0 | 0 | 95 | 50 | 5 | 0 | 0 | 0 | 0 |
| Sodium lauryl sulfate | 0 | 0 | 0 | 0 | 0 | 0 | 0 | 0 | 0 | 0 | 0 | 95 | 50 | 5 | 0 |
| Stearic acid | 0 | 0 | 0 | 0 | 0 | 0 | 0 | 0 | 0 | 0 | 0 | 0 | 0 | 0 | 95 |
| Igepal DM-970[3] | 0 | 0 | 0 | 0 | 0 | 0 | 0 | 0 | 0 | 0 | 0 | 0 | 0 | 0 | 0 |

| | Examples | | | | | | | | | | | | | | |
|---|---|---|---|---|---|---|---|---|---|---|---|---|---|---|---|
| | 17 | 18 | 19 | 20 | 21 | 22 | 23 | 24 | 25 | 26 | 27 | 28 | 29 | 30 | 31 |
| Tetradecyl dimethyl amine oxide dihydrate | 50 | 95 | 5 | 50 | 95 | 30 | 30 | 30 | 30 | 30 | 30 | 30 | 30 | 30 | 30 |
| Soap | 0 | 0 | 0 | 0 | 0 | 35 | 35 | 35 | 35 | 30 | 30 | 30 | 30 | 30 | 30 |
| Igepon AC-78[1] | 0 | 0 | 0 | 0 | 0 | 35 | 0 | 0 | 0 | 30 | 30 | 30 | 30 | 30 | 30 |
| Igepon TC-42[2] | 0 | 0 | 0 | 0 | 0 | 0 | 35 | 0 | 0 | 10 | 0 | 0 | 5 | 5 | 0 |
| Sodium dodecyl benzene sulfonate | 0 | 0 | 0 | 0 | 0 | 0 | 0 | 35 | 0 | 0 | 10 | 0 | 5 | 0 | 5 |
| Sodium lauryl sulfate | 0 | 0 | 0 | 0 | 0 | 0 | 0 | 0 | 0 | 0 | 0 | 0 | 0 | 0 | 0 |
| Stearic acid | 50 | 5 | 0 | 0 | 0 | 0 | 0 | 0 | 35 | 0 | 0 | 10 | 0 | 5 | 5 |
| Igepal DM-970[3] | 0 | 0 | 95 | 50 | 5 | 0 | 0 | 0 | 0 | 0 | 0 | 0 | 0 | 0 | 0 |

[1] GAF brand of sodium cocoyl isetheonate
[2] GAF brand of sodium cocoyl N-methyl taurate
[3] GAF brand dinonylphenol ethoxylate Other detergent bar formulations can be prepared following the above procedure using an appropriate trialkylamine oxide dihydrate and any of the many other components conventionally used in toilet soaps.

What is claimed is:

1. In a process for preparing a detergent bar suitable for use as toilet soap from a detergent bar formulation comprising a trialkylamine oxide, the improvement which comprises using as the trialkylamine oxide, in an amount such as to provide about 5-80% by weight of the detergent bar, a trialkylamine oxide dihydrate corresponding to the formula R'R''R'''NO.2H$_2$O wherein R' is a primary alkyl group containing 8-24 carbons, R'' is methyl, ethyl, or a primary alkyl group containing 8-24 carbons, and R''' is methyl or ethyl.

2. A process of claim 1 wherein said R'' and R''' are methyl groups.

3. A process of claim 2 wherein R' is a linear primary alkyl containing 12-24 carbon atoms.

4. A process of claim 3 further characterized by including the addition of a fatty acid soap to said detergent bar formulation.

5. A process of claim 4 which includes a synthetic detergent other than a trialkylamine oxide in said detergent bar formulation.

6. A process of claim 5 wherein said synthetic detergent is a sodium salt of a fatty acid amide of N-methyl tauride.

7. A process of claim 5 wherein said synthetic detergent is a sodium salt of a fatty acid ester of isethionic acid.

8. A process of claim 5 wherein said synthetic detergent is a sodium fatty alcohol sulfate.

9. A process of claim 3 further characterized by including the addition of a fatty acid to said detergent bar formulation.

* * * * *